(12) United States Patent
Jung et al.

(10) Patent No.: US 11,052,429 B2
(45) Date of Patent: Jul. 6, 2021

(54) PARTICLE SEPARATION APPARATUS

(71) Applicant: Research Cooperation Foundation of Yeungnam University, Gyeongsan (KR)

(72) Inventors: Jin Young Jung, Daegu (KR); Byeong Jun Lee, Daegu (KR)

(73) Assignee: Research Cooperation Foundation of Yeungnam University, Gyeongsan (KR)

( * ) Notice: Subject to any disclaimer, the term of this patent is extended or adjusted under 35 U.S.C. 154(b) by 414 days.

(21) Appl. No.: 16/089,298

(22) PCT Filed: Jul. 17, 2017

(86) PCT No.: PCT/KR2017/007638
§ 371 (c)(1),
(2) Date: Sep. 27, 2018

(87) PCT Pub. No.: WO2018/048087
PCT Pub. Date: Mar. 15, 2018

(65) Prior Publication Data
US 2020/0298279 A1    Sep. 24, 2020

(30) Foreign Application Priority Data

Sep. 12, 2016  (KR) .................... 10-2016-0117414

(51) Int. Cl.
*B07B 13/04* (2006.01)
*B07B 1/52* (2006.01)
(Continued)

(52) U.S. Cl.
CPC .............. *B07B 1/522* (2013.01); *B07B 13/04* (2013.01); *B07B 13/16* (2013.01); *C02F 3/12* (2013.01)

(58) Field of Classification Search
CPC ......... B07B 1/522; B07B 13/04; B07B 13/16; C02F 3/12; C02F 1/001; C02F 1/40;
(Continued)

(56) References Cited

U.S. PATENT DOCUMENTS 4,260,496 A * 4/1981 Beer .................... B01D 61/002
                                                                100/120
6,083,386 A * 7/2000 Lloyd ....................... C02F 9/00
                                                                119/527
(Continued)

FOREIGN PATENT DOCUMENTS

JP       58106398 A  *  6/1983  ............... F28G 1/12
JP       02251299 A  *  10/1990
(Continued)

OTHER PUBLICATIONS

International Search Report for PCT/KR2017/007638 filed on Jul. 17, 2017.

*Primary Examiner* — Patrick H Mackey

(57) ABSTRACT

Disclosed herein is a particle separation apparatus. The particle separation apparatus includes: a bioreactor; a first flow path through which the sludge is discharged from the bioreactor; a first filter including a first mesh separating the granular microorganisms contained in the sludge according to size; a second flow path into which an effluent having passed through the first filter flows; a third flow path connected to the second flow path to discharge the effluent outside; a fourth flow path connected to one side of the second flow path and mounted on a surface of the first filter connected to a surface of the first filter with the second flow path mounted thereon; a fifth flow path through which the effluent having been discharged from the fourth flow path and passed through the first filter flows into the bioreactor; and a first pump creating a flow of the effluent.

20 Claims, 13 Drawing Sheets

(51) Int. Cl.
*B07B 13/16* (2006.01)
*C02F 3/12* (2006.01)

(58) Field of Classification Search
CPC ...... B01D 63/068; B01D 63/00; B01D 33/15;
B01D 33/461; B01D 33/466; G01N 1/14;
G01N 2001/4088
See application file for complete search history.

(56) References Cited

U.S. PATENT DOCUMENTS

| | | | |
|---|---|---|---|
| 6,592,763 B1* | 7/2003 | Benedictus | C02F 3/1268 |
| | | | 210/652 |
| 7,678,268 B2* | 3/2010 | Smith | G01R 1/06738 |
| | | | 210/189 |
| 8,445,259 B2* | 5/2013 | Kang | C05F 17/40 |
| | | | 435/262 |
| 9,758,407 B2* | 9/2017 | Hsieh | C02F 3/1221 |
| 2013/0193056 A1* | 8/2013 | Tashiro | B01D 33/0067 |
| | | | 210/255 |
| 2020/0246732 A1* | 8/2020 | Jung | C02F 1/40 |
| 2020/0361804 A1* | 11/2020 | Wang | C02F 9/00 |

FOREIGN PATENT DOCUMENTS

| | | |
|---|---|---|
| JP | H02-251299 A | 10/1990 |
| JP | H07-313990 A | 12/1995 |
| JP | 2006-94821 A | 4/2006 |
| KR | 10-0693186 B1 | 3/2007 |
| KR | 10-0837698 B1 | 6/2008 |
| KR | 10-1163361 B1 | 7/2012 |
| KR | 10-1613711 B1 | 4/2016 |

* cited by examiner

[FIG. 1]
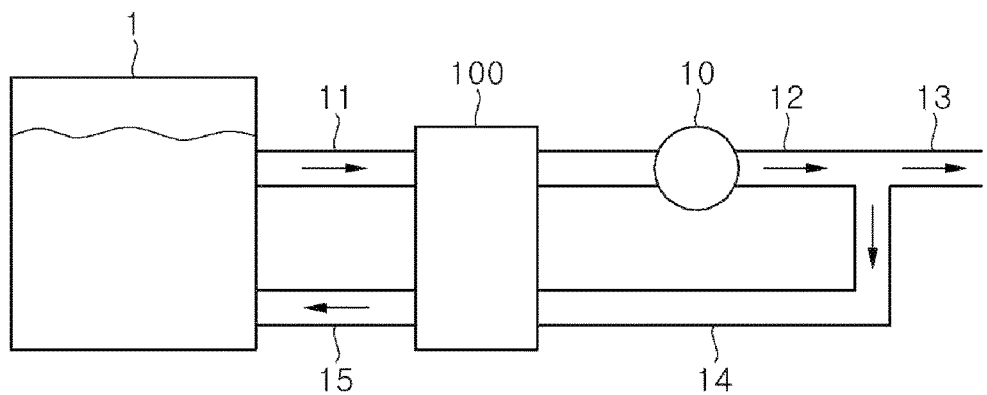
[FIG. 2]
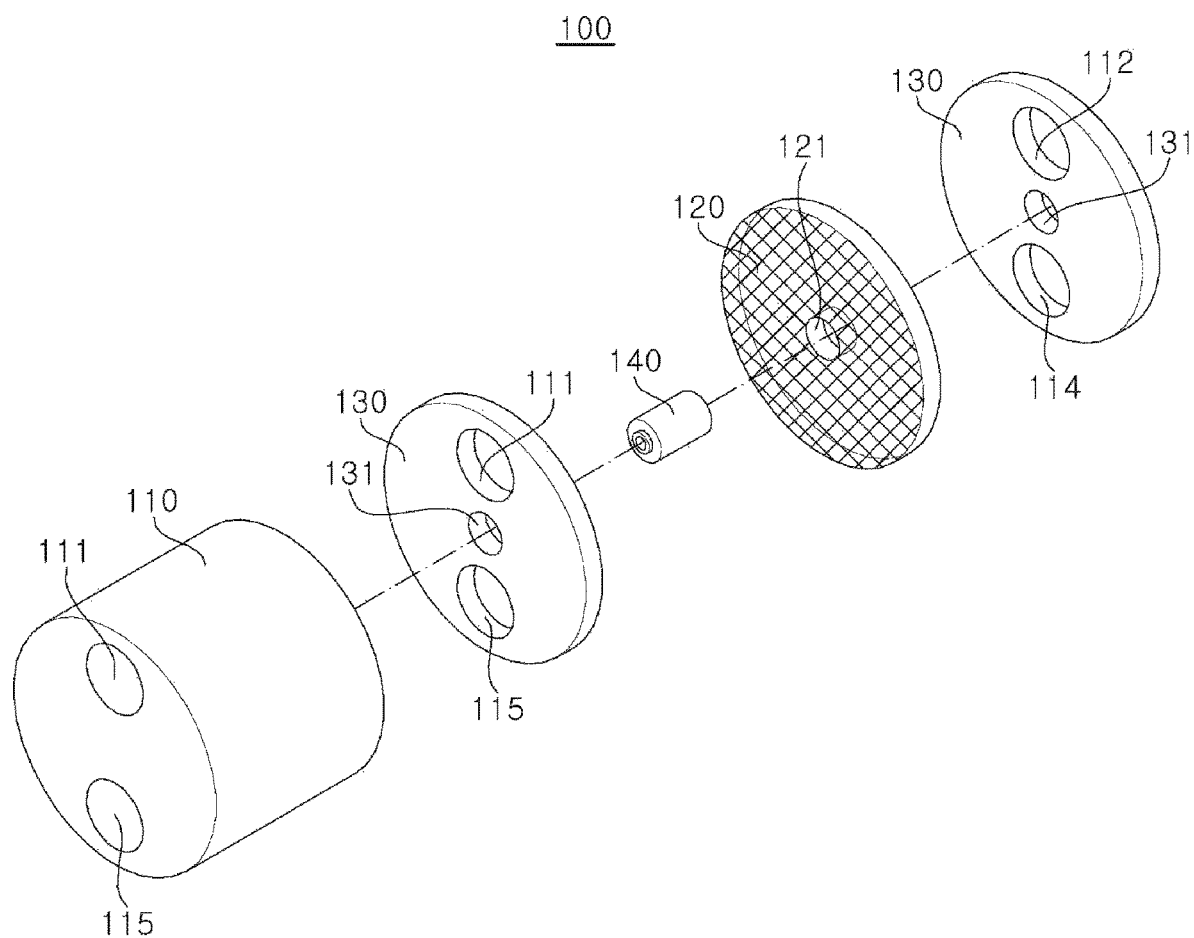

[FIG. 3]
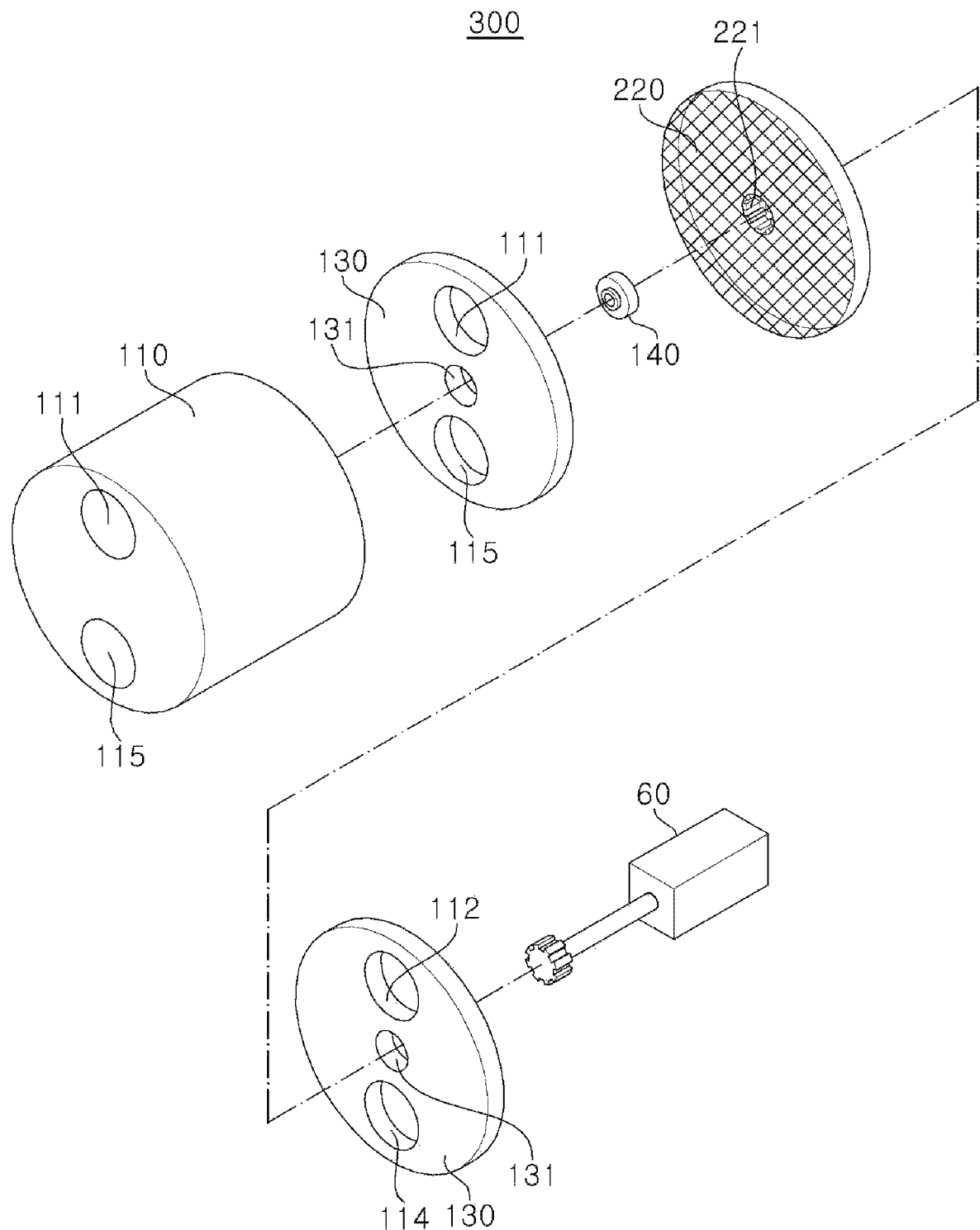

[FIG. 4]
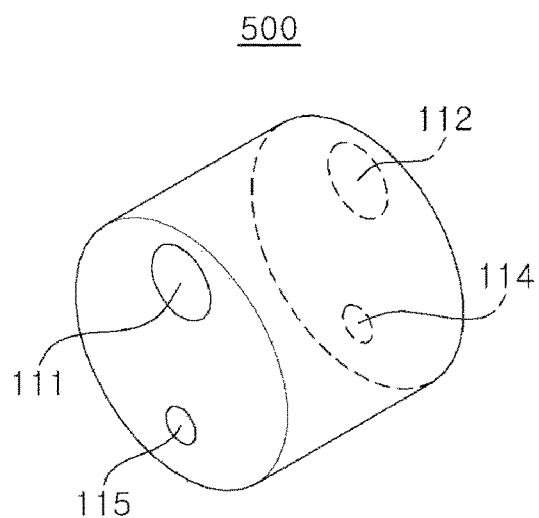
[FIG. 5]
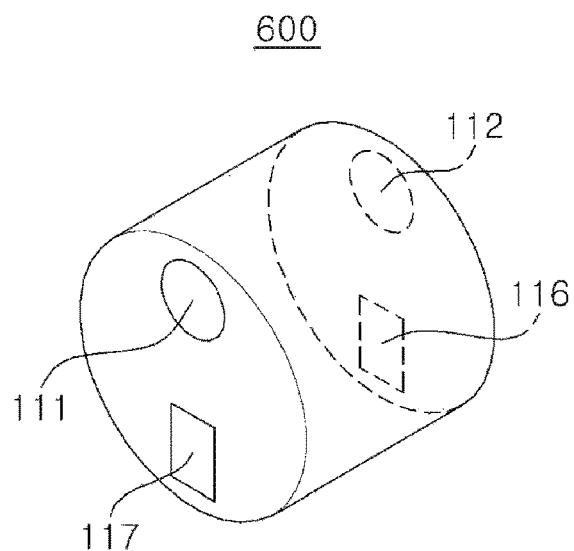
[FIG. 6]
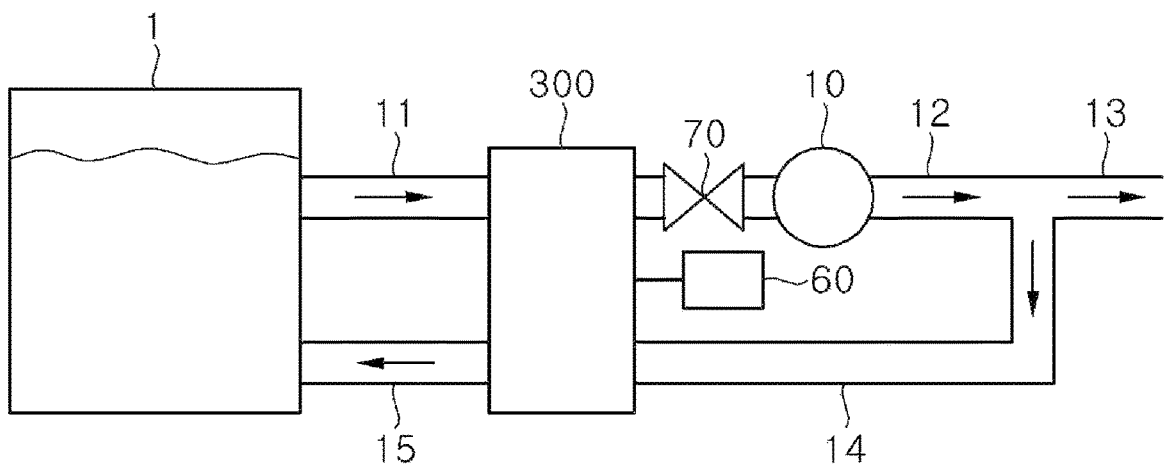

[FIG. 7]
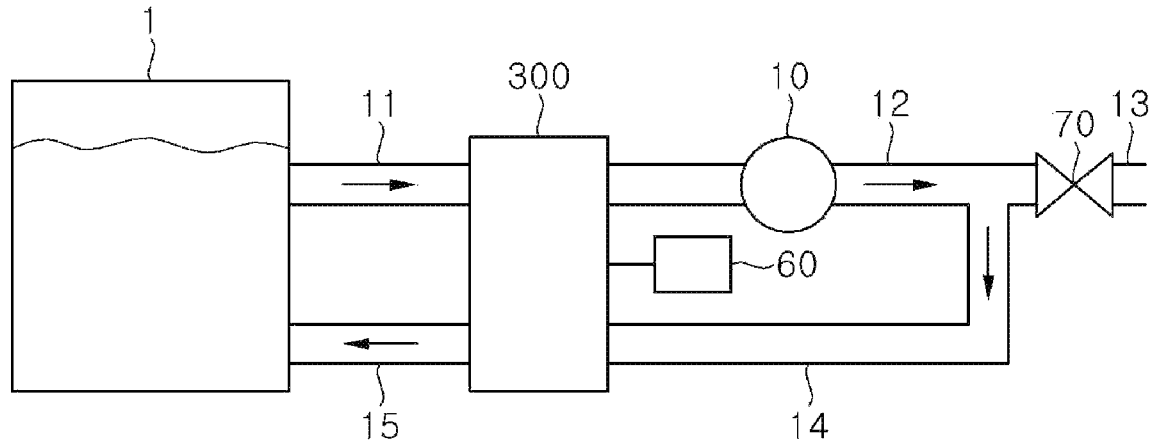
[FIG. 8]
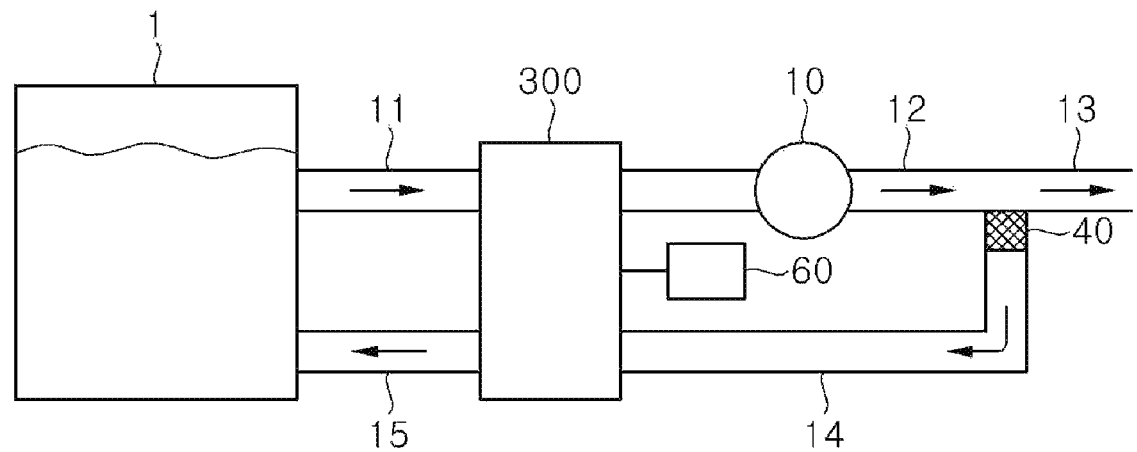
[FIG. 9]
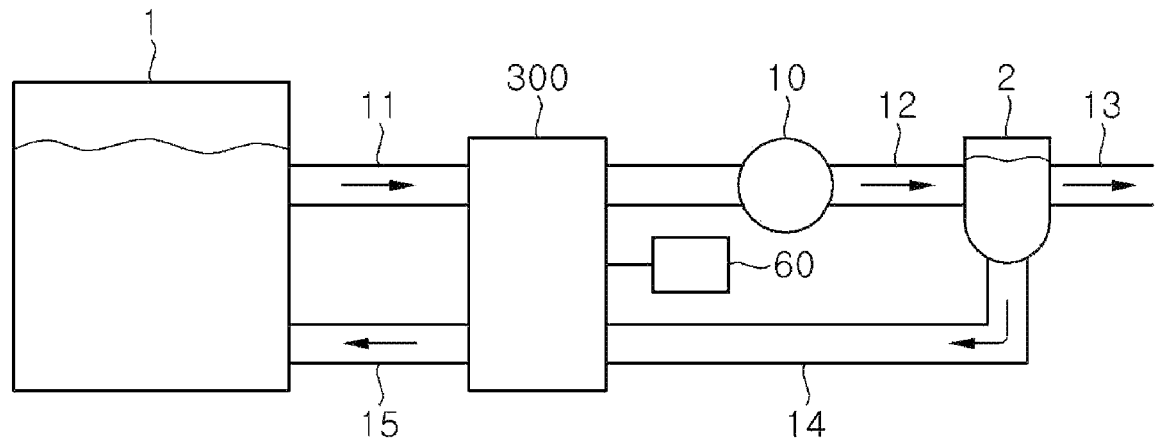

[FIG. 10]
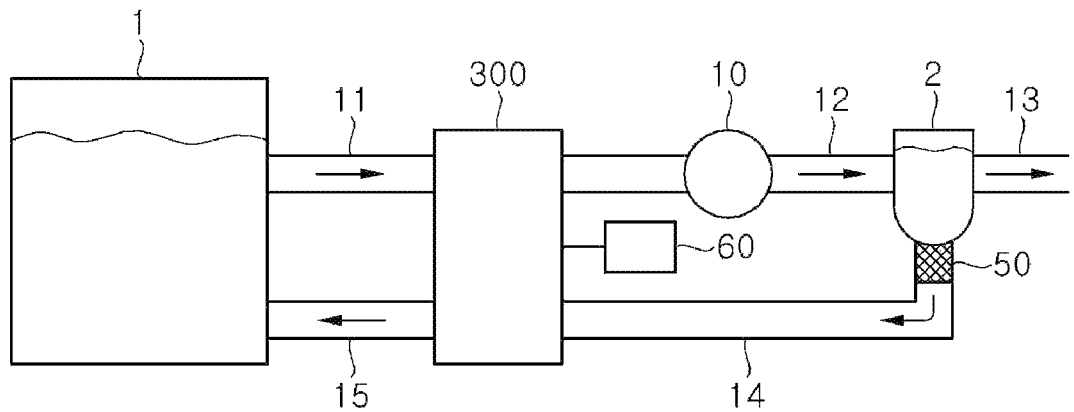
[FIG. 11]
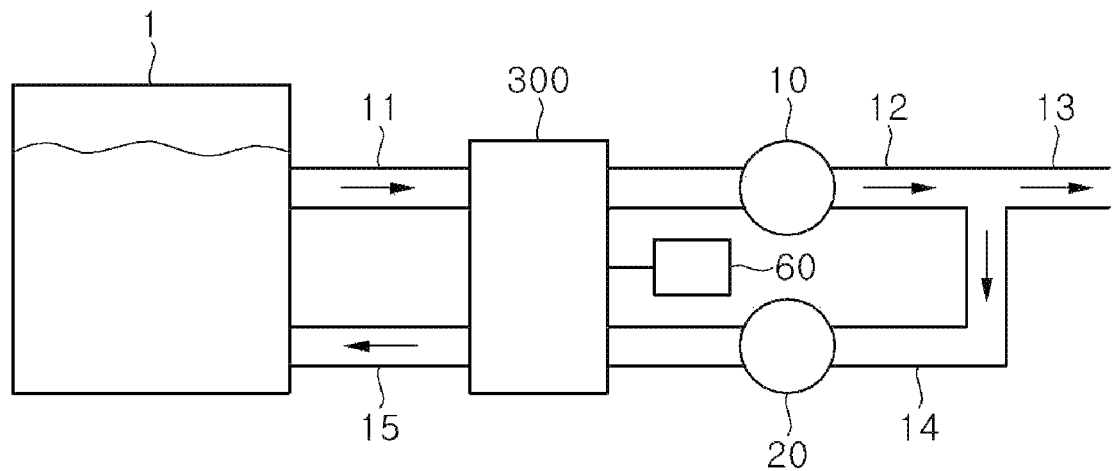
[FIG. 12]
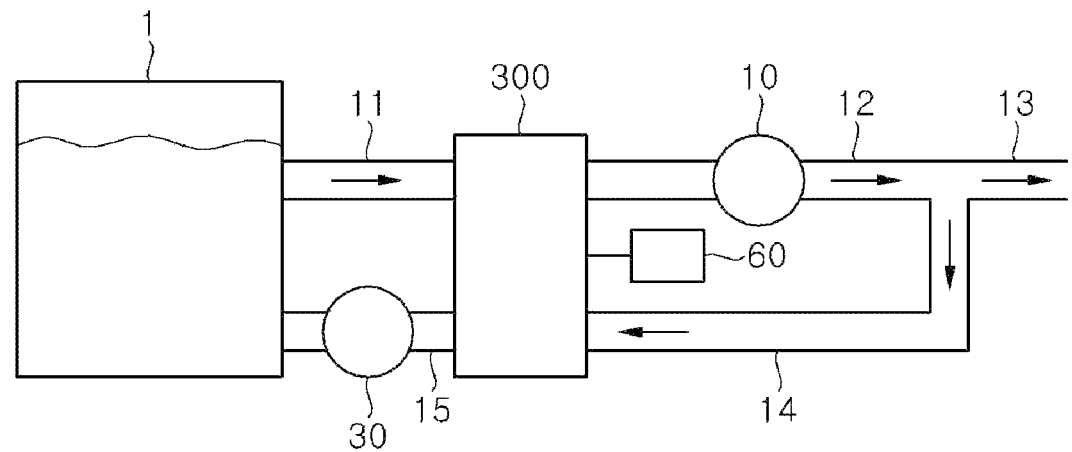

[FIG. 13]
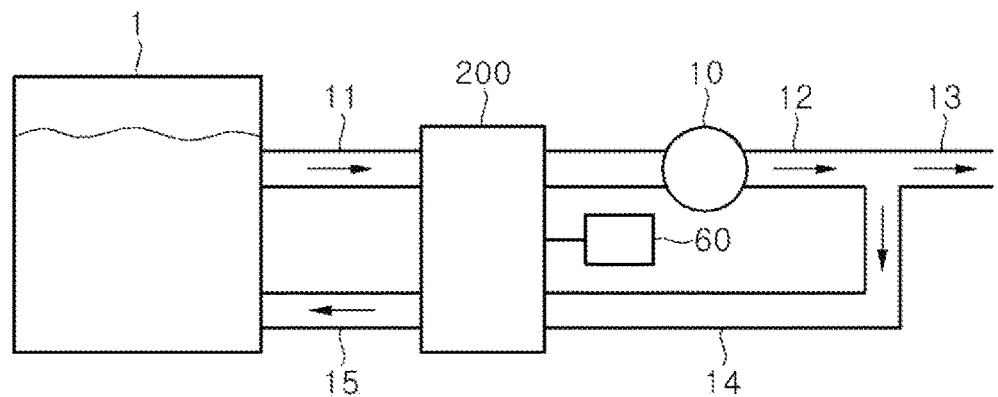
[FIG. 14]
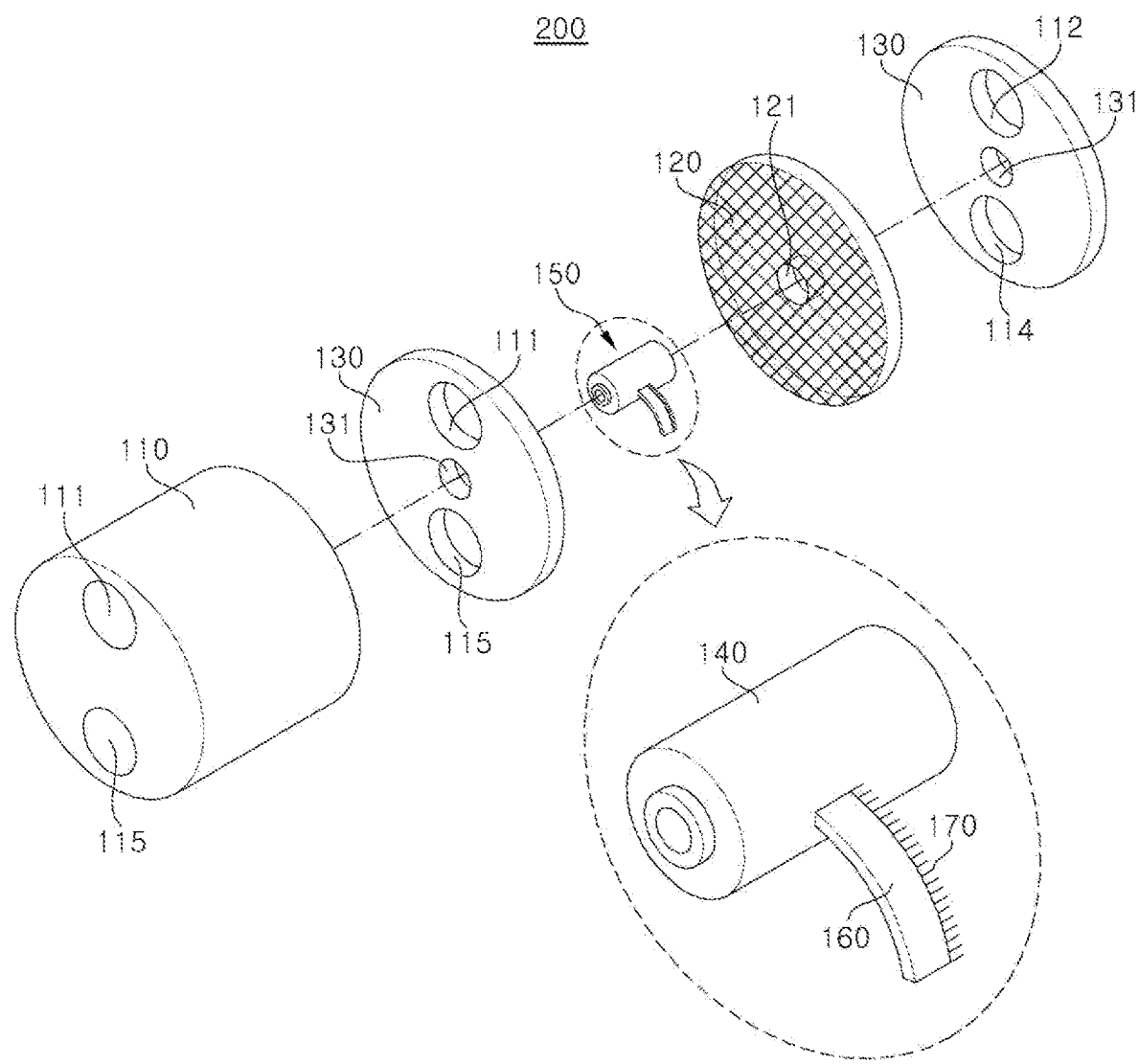

【FIG. 15】
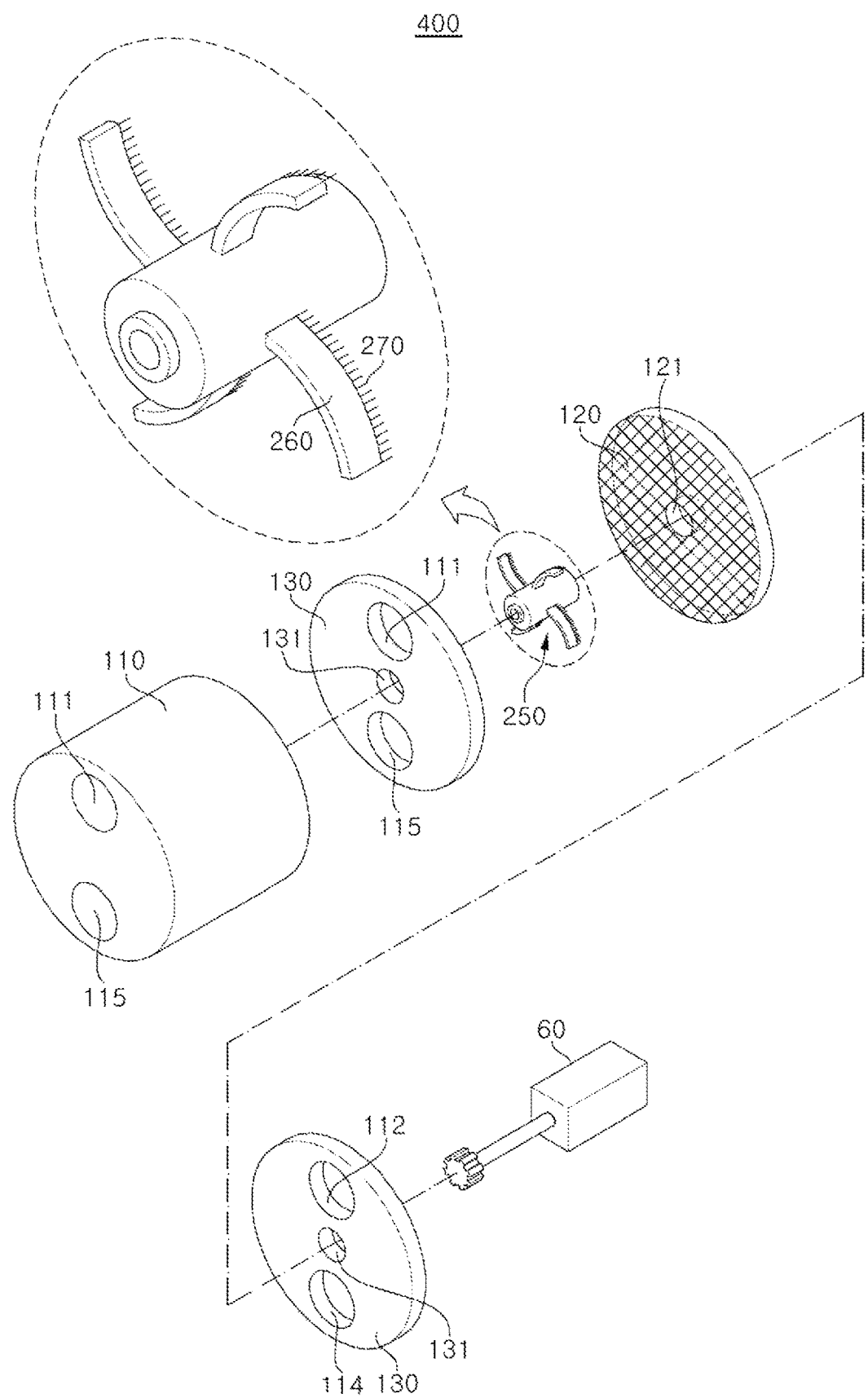

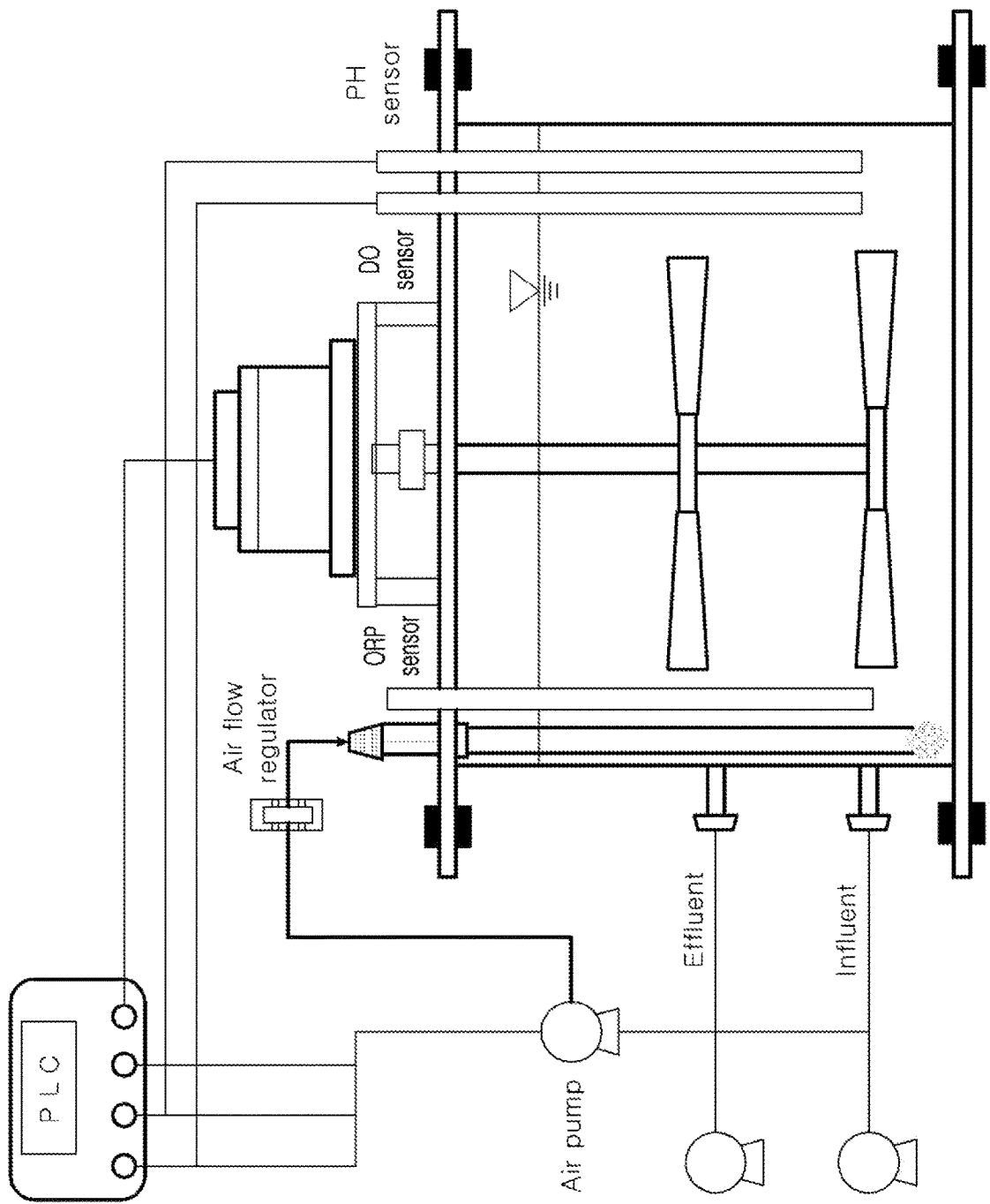
[FIG. 16]

[FIG. 17]
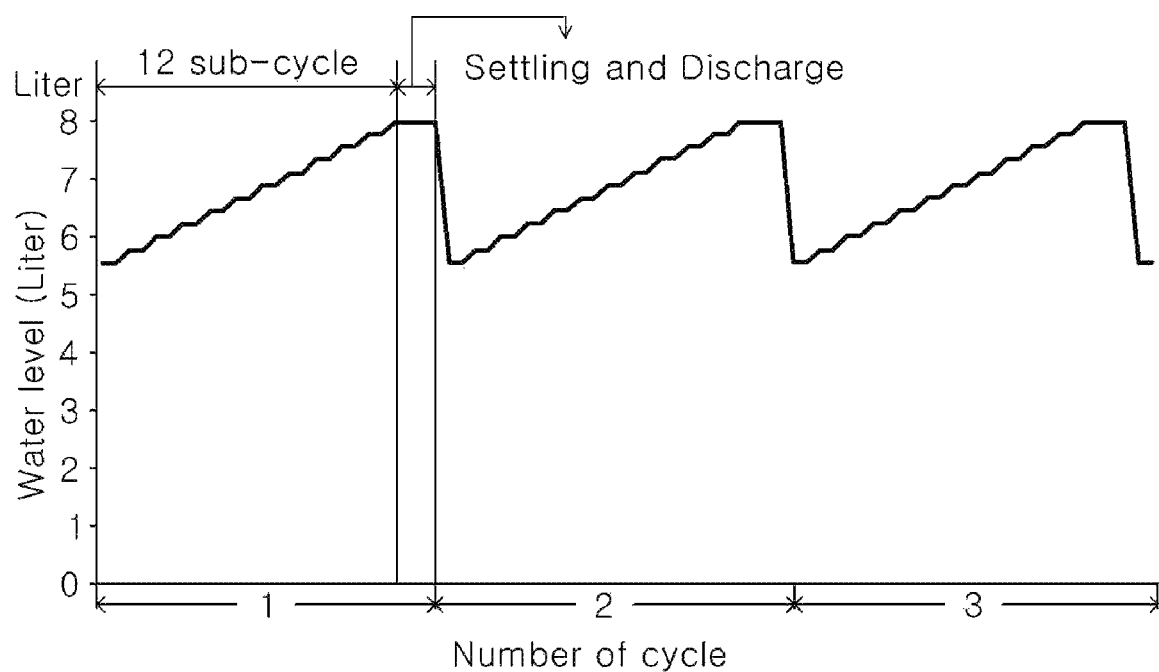

[FIG. 18]
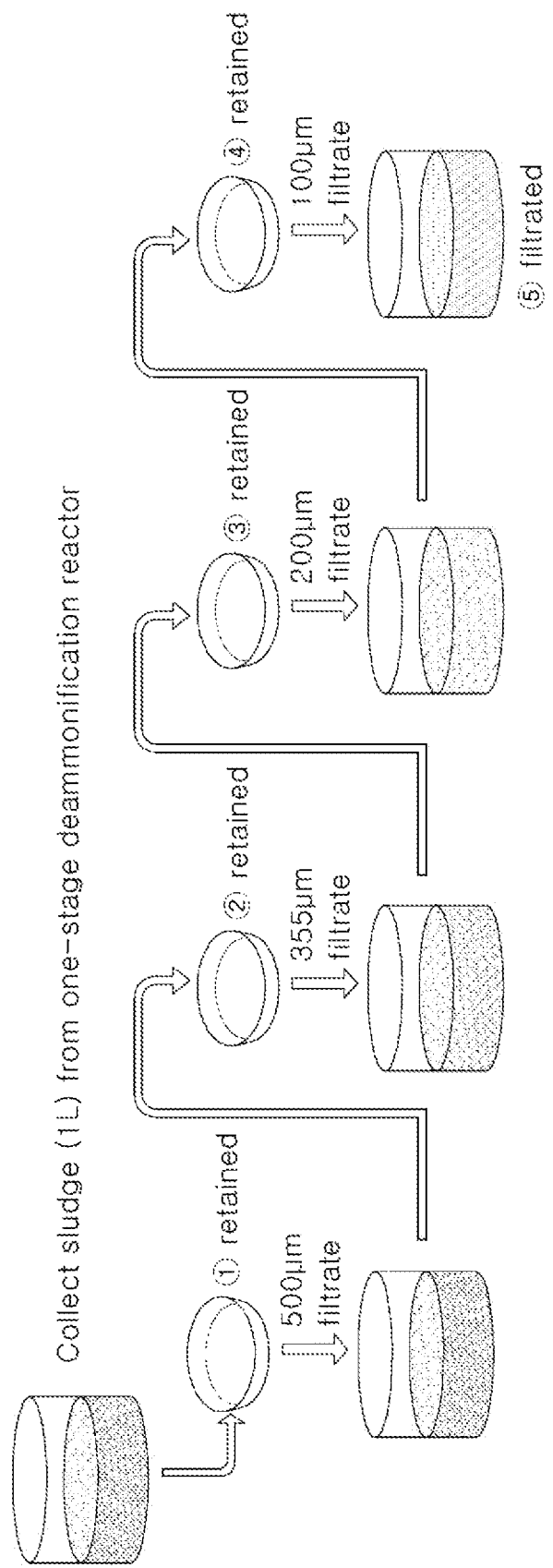

[FIG. 19]
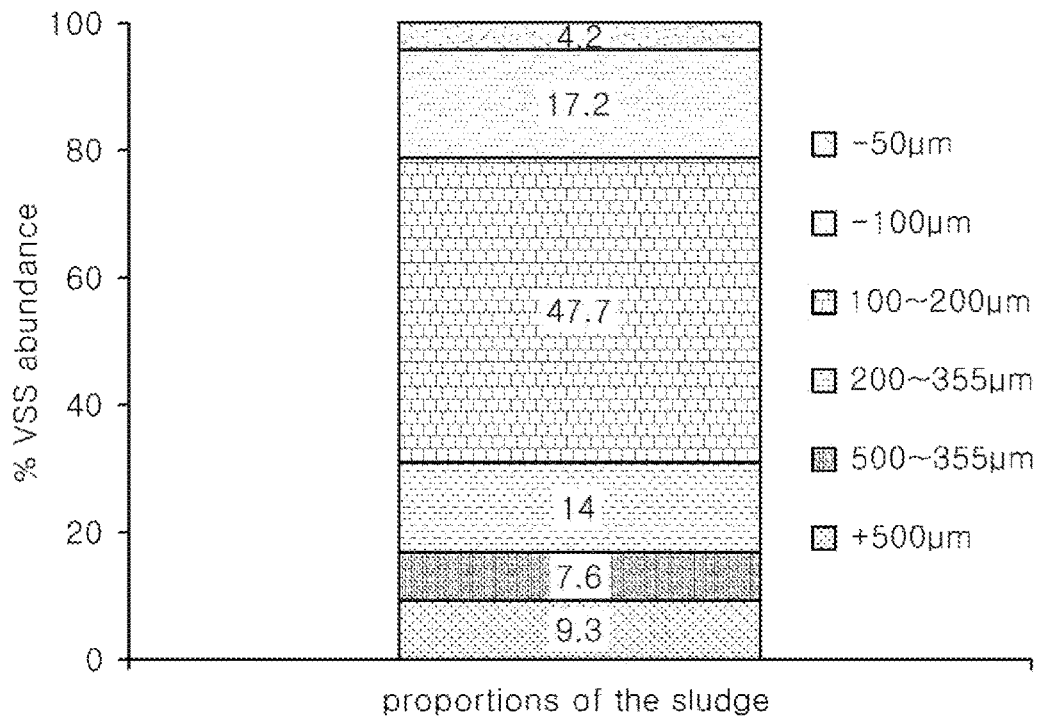
[FIG. 20]
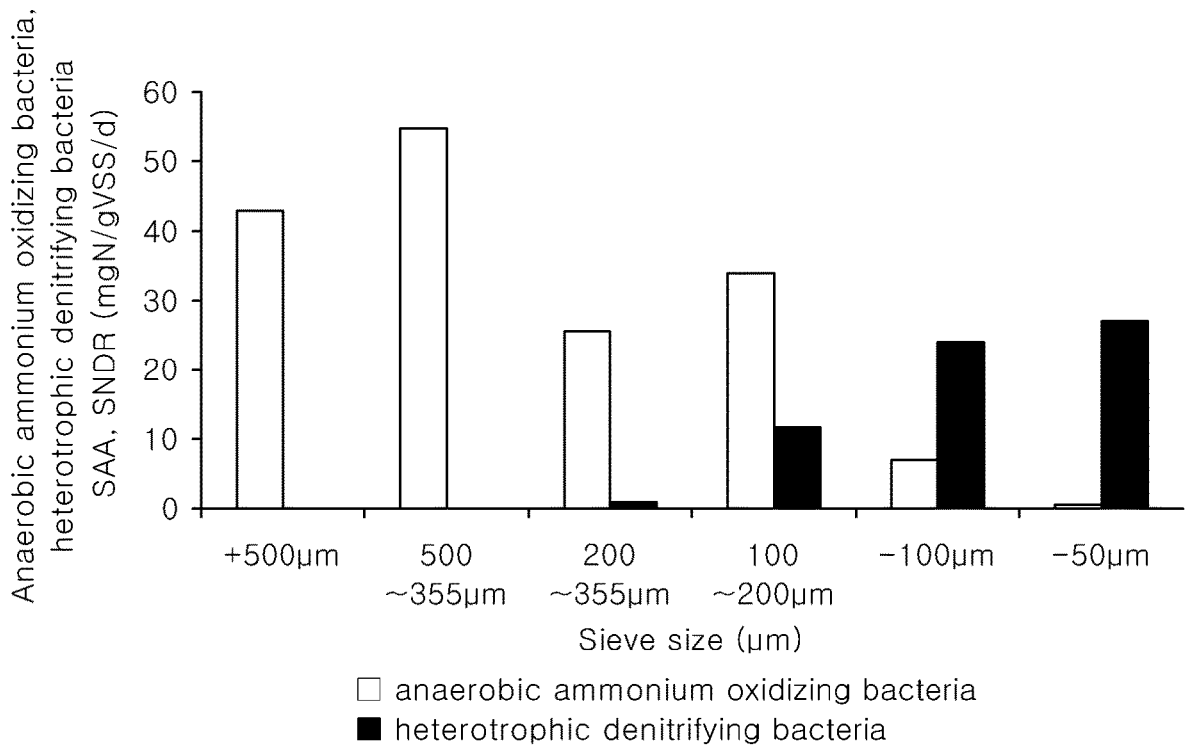

[FIG. 21]
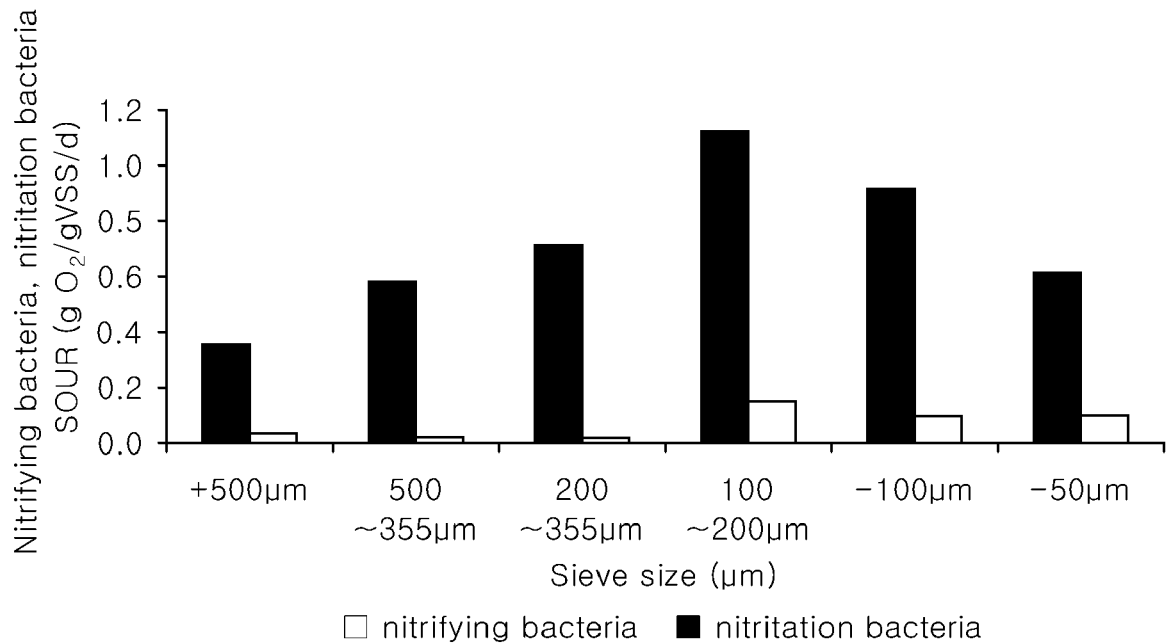
[FIG. 22]
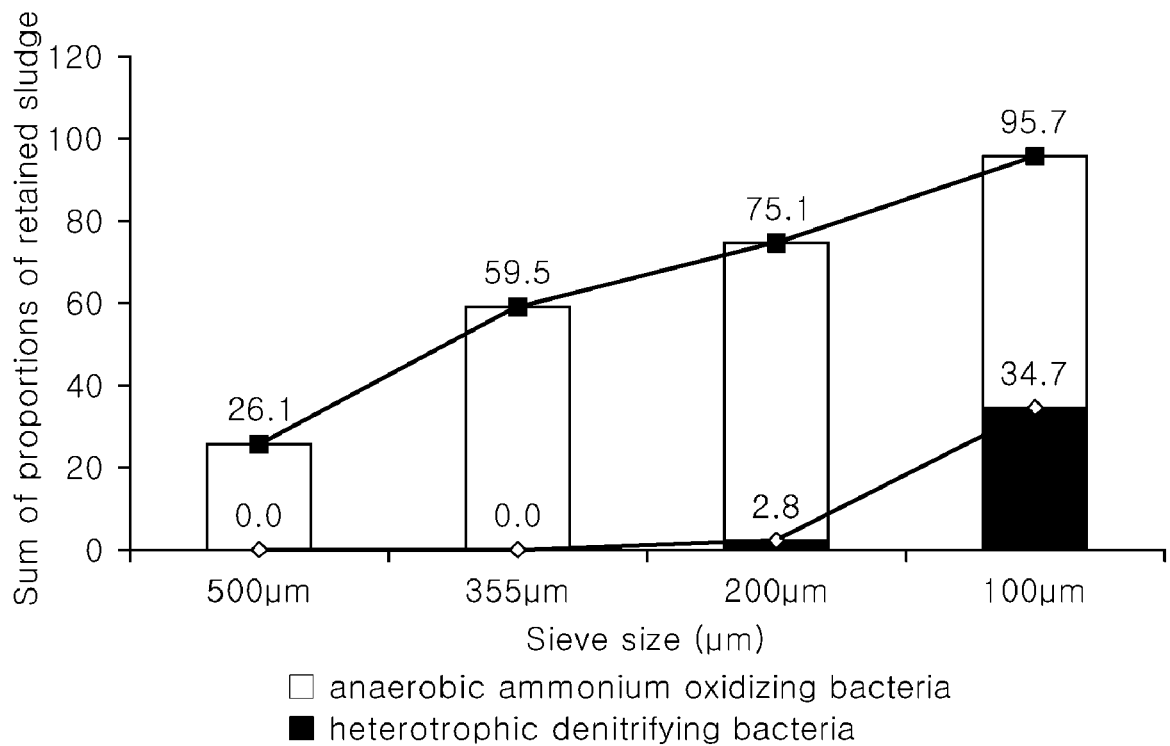

【FIG. 23】
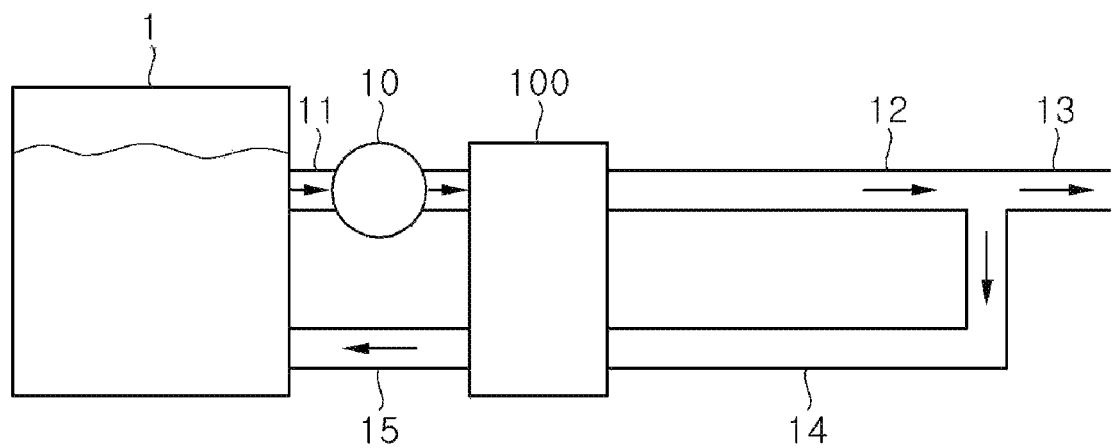
【FIG. 24】
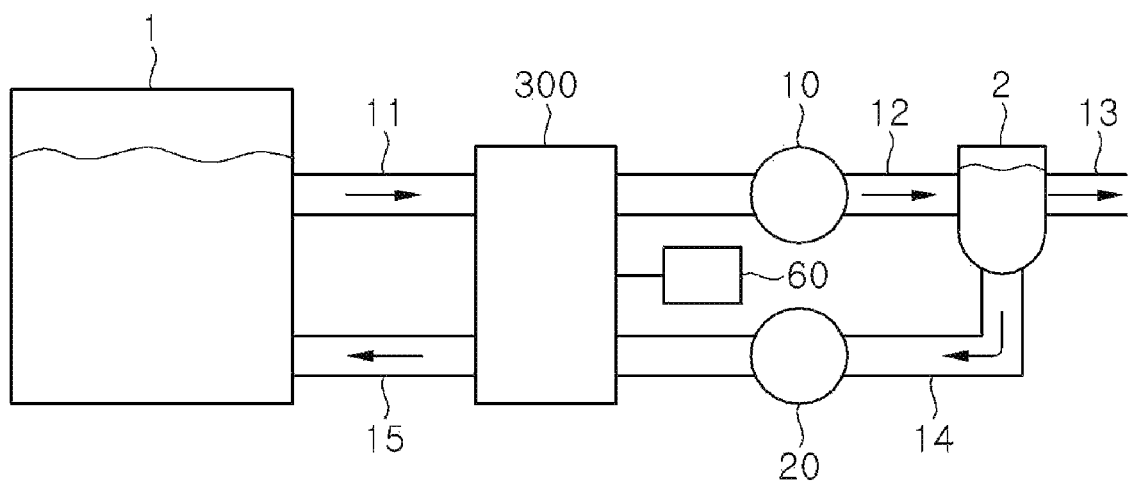

PARTICLE SEPARATION APPARATUS

CROSS-REFERENCE TO RELATED APPLICATIONS

The present application is a U.S. National Stage of International Patent Application No. PCT/KR2017/007638 filed Jul. 17, 2017, which claims priority to and the benefit of Korean Patent Application No. 10-2016-0117414 filed in the Korean Intellectual Property Office on Sep. 12, 2016, the entire contents of which are incorporated herein by reference.

TECHNICAL FIELD

The present invention relates to a particle separation apparatus and, more particularly, to a particle separation apparatus which can selectively separate a specific microorganism from various species of microorganisms having different particle sizes in a bioreactor and discharge the separated specific microorganism from the bioreactor.

BACKGROUND ART

At today's industrial sites where a variety of eco-friendly processes are used, wastewater treatment remains a challenge.

Particularly, nitrogen removal is accomplished by various methods including physicochemical processes such as degassing or ammonification and biological processes such as nitrification, denitrification, or vegetational absorption and adsorption. Thereamong, biological nitrification-denitrification is a nitrogen removal process which is most widely used.

In the 1990s, anaerobic ammonium oxidation (anammox) was introduced as a way of nitrogen removal. Recently, anammox is called a deammonification process in combination with partial nitritation, which is a pretreatment process. More than 100 full-scale deammonification processes had been reported by 2015. About 50% or more of full-scale deammonification processes in practical use are based on a sequencing batch reactor (SBR) process in which nitritation and anammox are simultaneously performed in a single reactor and accompanied by heterotrophic denitrification for removal of nitrate, which is a by-product of nitritation.

The following reaction schemes 1 to 3 show a nitrogen removal route in which partial nitration, anammox, and heterotrophic denitrification are performed in a single reactor.

$$NH_4^+ + 0.75O_2 + HCO_3^- \rightarrow 0.5NH_4^+ + 0.5NO_2^- + 1.5H_2O + CO_2 \qquad \text{[Reaction Scheme 1]}$$

$$NH_4^+ + 1.32NO_2^- + 0.066HCO_3^- + 0.13H^+ \rightarrow 0.26NO_3^- + 1.02N_2 + 0.066CH_2O_{0.5}N_{0.15} + 2.03H_2O \qquad \text{[Reaction Scheme 2]}$$

$$0.26NO_3^- + 0.22H_3OH + 0.04CO_2 \rightarrow 0.13N^2 + 0.26HCO_3^- + 0.3H_2O \qquad \text{[Reaction Scheme 3]}$$

In such a deammonification process in the single reactor, it is desirable that partial nitrite and anammox be dominant while heterotrophic denitrification be a side reaction by which $NO_3^-$, which is a by-product produced according to Reaction Scheme 2, is additionally removed. However, since anaerobic ammonium oxidizing bacteria involved in Reaction Scheme 1 have an extremely low growth rate (doubling time: about 11 days) and an extremely low cell yield (0.13 g-dry weight/g-$NH_4$—N), as compared with other microorganisms, when the anaerobic ammonium oxidizing bacteria are not dominant in the reactor, $NO_2^-$ to be eliminated through Reaction Scheme 2 is consumed by heterotrophic denitrifying bacteria, which have a higher growth rate, as shown in Reaction Scheme 4, such that nitrogen removal in the single reactor cannot be performed smoothly.

$$6NO_2^- + 3CH3OH + 3CO_2 \rightarrow 3N_2 + 6HCO_3^- + 3H_2O \qquad \text{[Reaction Scheme 4]}$$

In addition, since there is substrate competition for $NO_2^-$ between nitrification and anammox, as shown in Reaction Scheme 5, nitrifying bacteria, which induce nitrification rather than partial nitritation, need to be continuously removed from the reactor.

$$NO_2^- + 0.5O_2 \rightarrow NO_3^- \qquad \text{[Reaction Scheme 5]}$$

On the other hand, anaerobic ammonium oxidizing bacteria have low resistance to oxygen and thus are commonly present inside a membrane formed of nitritation bacteria. Thus, anaerobic ammonium oxidizing bacteria can be present in granular form.

Conventionally, a hydrocyclone has been widely used to separate anaerobic ammonium oxidizing bacteria from heterotrophic denitrifying bacteria in a wastewater treatment system. However, since such a hydrocyclone exhibits very low efficiency in separating the anaerobic ammonium oxidizing bacteria and the heterotrophic denitrifying bacteria from one another, which are not significantly different from one another in terms of fluid resistance or weight, and is operable only under fixed conditions, it is difficult to use the hydrocyclone in industrial facilities.

Therefore, there is a need for an apparatus used in deammonification in a single bioreactor, which can allow heterotrophic denitrifying bacteria and nitrifying bacteria to be separated and discharged outside the bioreactor so as to allow anaerobic ammonium oxidizing bacteria, specifically granular microorganisms formed of the anaerobic ammonium oxidizing bacteria and nitritation bacteria, to be separated and concentrated in the bioreactor, thereby improving nitrogen removal efficiency.

DISCLOSURE

Technical Problem

The present invention is aimed at providing a particle separation apparatus which can allow granular microorganisms present in a single reactor to be selectively separated according to size to be concentrated in the reactor or to be discharged outside the reactor.

Technical Solution

It is one aspect of the present invention to provide a particle separation apparatus which can allow granular microorganisms present in a single reactor to be selectively separated according to size to be concentrated in the reactor or to be discharged outside the reactor.

In accordance with one aspect of the present invention, a particle separation apparatus includes: a bioreactor storing a sludge containing granular microorganisms; a first flow path through which the sludge is discharged from the bioreactor; a first filter including a first mesh separating the granular microorganisms contained in the sludge discharged through the first flow path according to size; a second flow path into which an effluent having passed through the first filter flows; a third flow path connected to the second flow path to discharge the effluent outside; a fourth flow path connected to one side of the second flow path and mounted on a surface of the first filter connected to a surface of the first filter with the second flow path mounted thereon to circulate the effluent to the bioreactor; a fifth flow path through which the effluent having been discharged from the fourth flow path and passed through the first filter flows into the bioreactor; and a first pump creating a flow of the effluent, wherein the first mesh unit is rotatably mounted on the first filter.

In accordance with another aspect of the present invention, a particle separation apparatus includes: a bioreactor storing a sludge containing granular microorganisms; a first flow path through which the sludge is discharged from the bioreactor; a fourth filter including a first mesh separating the granular microorganisms contained in the sludge discharged through the first flow path according to size and a blade assembly rotatably mounted on a surface of the first mesh; a second flow path through which an effluent having passed through the fourth filter is discharged outside; a third flow path connected to the second flow path to discharge the effluent outside; a fourth flow path connected to one side of the second flow path and mounted on a surface of the fourth filter connected to a surface of the fourth filter with the second flow path mounted thereon to circulate the effluent to the bioreactor; a fifth flow path through which the effluent having been discharged from the fourth flow path and passed through the first filter flows into the bioreactor; and a first pump creating a flow of the effluent, wherein the blade assembly includes a rotary blade.

Advantageous Effects

According to the present invention, with the first mesh provided to the filter and having a specific pore diameter, the particle separation apparatus can allow anaerobic ammonium oxidizing bacteria to be separated and concentrated through a continuous process while allowing heterotrophic denitrifying bacteria to be separated and discharged from a bioreactor through a continuous process, thereby improving nitrogen removal efficiency.

In addition, with the second mesh and/or the third mesh further provided, the particle separation apparatus can prevent heterotrophic denitrifying bacteria in an effluent discharged from the bioreactor from flowing back into the bioreactor.

DESCRIPTION OF DRAWINGS

FIG. 1 is a diagram of a particle separation apparatus according to one exemplary embodiment of the present invention.

FIG. 2 and FIG. 3 are exploded perspective views of first filters according to exemplary embodiments of the present invention, respectively.

FIG. 4 and FIG. 5 are views of housings according to exemplary embodiments of the present invention, respectively.

FIG. 6 to FIG. 13 are diagrams of particle separation apparatuses according to other exemplary embodiments of the present invention, respectively.

FIG. 14 and FIG. 15 are exploded perspective views of fourth filters according to exemplary embodiments of the present invention, respectively.

FIG. 16 is a view of a bioreactor according to one exemplary embodiment of the present invention.

FIG. 17 is a diagram illustrating a method of controlling operation of a bioreactor according to one exemplary embodiment of the present invention.

FIG. 18 is a diagram illustrating steps of a process of sieving microorganisms according to one embodiment of the present invention.

FIG. 19 is a graph showing size-dependent distribution of granular microorganisms in a bioreactor according to one exemplary embodiment of the present invention.

FIG. 20 is a graph showing changes in activity of anaerobic ammonium oxidizing bacteria and heterotrophic denitrifying bacteria depending on the size distribution of granular microorganisms in a bioreactor according to one exemplary embodiment of the present invention.

FIG. 21 is a graph showing changes in activity of nitrifying bacteria and nitritation bacteria depending on the size distribution of granular microorganisms in a bioreactor according to one exemplary embodiment of the present invention.

FIG. 22 is a graph showing cumulative activity of microorganisms depending on sieving pore size according to one exemplary embodiment of the present invention.

FIG. 23 to FIG. 24 are diagrams of particle separation apparatuses according to other exemplary embodiments of the present invention, respectively.

BEST MODE

It should be understood that the present invention may be embodied in different ways and is not limited to the following embodiments, which are provided for complete disclosure and thorough understanding of the present invention by those skilled in the art.

Herein, spatially relative terms such as "upper" and "lower" are defined with reference to the accompanying drawings. Thus, it will be understood that the term "upper surface" can be used interchangeably with the term "lower surface", and when an element such as a layer or a film is referred to as being placed "on" another element, it can be directly placed on the other element, or intervening element(s) may be present. On the other hand, when an element is referred to as being placed "directly on" another element, there are no intervening element(s) therebetween.

Like components will be denoted by like reference numerals throughout the specification. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof.

As used herein, the term "effluent" is not limited to an effluent passing through a specific flow path and may refer to all fluids passing through a first flow path 11, a second flow path 12, a third flow path 13, a fourth flow path 14, and a fifth flow path 15 which are connected to a bioreactor storing a sludge containing various granular microorganisms.

Hereinafter, exemplary embodiments of the present invention will be described in detail with reference to the accompanying drawings.

In accordance with one aspect of the present invention, a particle separation apparatus includes: a bioreactor storing a sludge containing granular microorganisms; a first flow path through which the sludge is discharged from the bioreactor; a first filter including a first mesh separating the granular microorganisms contained in the sludge discharged through the first flow path according to size; a second flow path into which an effluent having passed through the first filter flows; a third flow path connected to the second flow path to discharge the effluent outside; a fourth flow path connected to one side of the second flow path and mounted on a surface of the first filter connected to a surface of the first filter with the second flow path mounted thereon to circulate the effluent to the bioreactor; a fifth flow path through which the effluent having been discharged from the fourth flow path and passed through the first filter flows into the bioreactor; and a first pump creating a flow of the effluent, wherein the first mesh unit is rotatably mounted on the first filter.

In accordance with another aspect of the present invention, a particle separation apparatus includes: a bioreactor storing a sludge containing granular microorganisms; a first flow path through which the sludge is discharged from the bioreactor; a fourth filter including a first mesh separating the granular microorganisms contained in the sludge discharged through the first flow path according to size and a blade assembly rotatably mounted on a surface of the first mesh; a second flow path through which an effluent having passed through the fourth filter is discharged outside; a third flow path connected to the second flow path to discharge the effluent outside; a fourth flow path connected to one side of the second flow path and mounted on a surface of the fourth filter connected to a surface of the fourth filter with the second flow path mounted thereon to circulate the effluent to the bioreactor; a fifth flow path through which the effluent having been discharged from the fourth flow path and passed through the first filter flows into the bioreactor; and a first pump creating a flow of the effluent, wherein the blade assembly includes a rotary blade.

In some embodiments, the first mesh may have a pore diameter of 50 µm to 500 µm.

The blade assembly may include a cleaning brush attached to one side of the blade, wherein the cleaning brush may be rotated while contacting one surface of the first mesh upon rotation of the blade.

A first flow path connection connected to one side of the first filter or the fourth filter may have a larger area than a fourth flow path connection connected to one side of the first filter or the fourth filter.

In some embodiments, the second flow path may contact the first pump.

The particle separation apparatus may further include a second pump disposed on the fourth flow path upstream of the first filter or the fourth filter.

The particle separation apparatus may further include a third pump disposed on the fifth flow path upstream of the bioreactor.

The particle separation apparatus may further include a detention tank storing the effluent discharged from the second flow path, such that the effluent from the detention tank flows into the bioreactor through the fourth flow path or is discharged outside the particle separation apparatus through the third flow path.

In some embodiments, the granular microorganisms may include at least one selected from the group consisting of anaerobic ammonium oxidizing bacteria, heterotrophic denitrifying bacteria, nitritation bacteria, and nitrifying bacteria.

The anaerobic ammonium oxidizing bacteria may have a particle size of 100 µm or more, and each of the heterotrophic denitrifying bacteria and the nitrifying bacteria may have a particle size of less than 100 µm.

The particle separation apparatus may further include a sample collection valve mounted on the second flow path to perform component analysis on the microorganisms discharged from the bioreactor.

In some embodiments, the particle separation apparatus may further include a sample collection valve mounted on the third flow path to perform component analysis on the microorganisms discharged from the particle separation apparatus.

In some embodiments, the particle separation apparatus may further include a second filter disposed at a side of the second flow path connected to the fourth flow path, wherein the second filter may include a second mesh having a pore diameter of 1 µm to 50 µm.

The second filter may include a blade assembly rotatably mounted on a surface of the second mesh.

In some embodiments, the particle separation apparatus may further include a third filter disposed at an entrance of the fourth flow path connected to the detention tank, wherein the third filter may include a third mesh having a pore diameter of 1 µm to 50 µm.

The third filter may include a blade assembly rotatably mounted on a surface of the third mesh.

In some embodiments, the first filter may further include a blade assembly secured to a surface of the first mesh.

The bioreactor may contain anaerobic ammonium oxidizing bacteria performing anammox, wherein the anaerobic ammonium oxidizing bacteria may include at least one selected from the group consisting of *Candidatus Brocadia anammoxidans, Candidatus Kuenenia stuttgartiensis, Candidatus Scalindua wagneri, Candidatus Anammoxoglobus propionicus*, and *Planctomycete KSU*-1.

In addition, the bioreactor may contain nitritation bacteria performing nitritation and heterotrophic denitrifying bacteria performing heterotrophic denitrification, wherein the nitritation bacteria may include at least one selected from the group consisting of *Nitrosomonas europaea, Nitrosococcus mobilis, Nitrosomonas nitrosa*, and *Nitrosomonas cryotolerans*, and the heterotrophic denitrifying bacteria may include at least one selected from the group consisting of *Pseudomonas, Bacillus, Spirillum, Hyphomicrobium, Agrobacterium, Acinetobacter, Propionobacterium, Rhizobium, Cornebacterium, Cytophata, Thiobacillus, Alcaligenes, Pseudomonas fluorescens, P. Aeruginosa, P. denitrificans, Alcaligenes* sp. *Curvibacter delicatus, Acidovorax defluvii, Dokdonella koreensis, Dokdonella koreensis, Flavobacterium limicola, Terrimonas ferruginea*, and *Terrimonas lutea*.

In some embodiments, the heterotrophic denitrifying bacteria and the nitrifying bacteria may be discharged to the second flow path through the first mesh.

Granules formed of the anaerobic ammonium oxidizing bacteria and the nitritation bacteria may be present in the bioreactor.

The granular microorganisms may be separated according to size by the first mesh and discharged outside the bioreactor through the second flow path.

In accordance with a further aspect of the invention, there is provided a particle separation system including the particle separation apparatus according to the invention, wherein the granular microorganisms include at least one selected from the group consisting of anaerobic ammonium oxidizing bacteria, heterotrophic denitrifying bacteria, nitritation bacteria, and nitrifying bacteria, and the particle separation system separates the granular microorganisms according to size and allows the separated granular microorganisms to be discharged outside the bioreactor or to be concentrated in the bioreactor.

In some embodiments, the granular microorganisms may include granules formed of the anaerobic ammonium oxidizing bacteria and the nitritation bacteria.

The particle separation system may be operated to prevent the granules formed of the anaerobic ammonium oxidizing bacteria and the nitritation bacteria from passing through the first mesh while allowing the nitrifying bacteria to pass through the first mesh.

The particle separation system may be operated such that 80 vol % or more of the granules formed of the anaerobic ammonium oxidizing bacteria and the nitritation bacteria can be concentrated in the bioreactor, based on the total volume of the granules.

As described above, anaerobic ammonium oxidizing bacteria, nitritation bacteria, heterotrophic denitrifying bacteria, and nitrifying bacteria are contained in the bioreactor 1 in which a deammonification process is performed. If the anaerobic ammonium oxidizing bacteria are not dominant, the heterotrophic denitrifying bacteria and the nitrifying bacteria become dominant, causing deterioration in nitrogen removal efficiency.

Thus, the present inventors utilized ecological characteristics of anaerobic ammonium oxidizing bacteria so as to allow the anaerobic ammonium oxidizing bacteria to be dominant in the deammonification process in a single reactor containing various species of microorganisms.

Specifically, it is necessary to control the sludge retention time (SRT) for each microorganism in the deammonification process in the single reactor. Considering the growth rate of each microorganism, a proper SRT for each microorganism is as shown in Table 1.

TABLE 1

| Kind of microorganism | Proper SRT |
| --- | --- |
| Anaerobic ammonium oxidizing bacteria | 50 days or more |
| Nitritation bacteria | 10 days or less |
| Heterotrophic denitrifying bacteria | 3 days or less |
| Nitrifying bacteria | Requiring continuous inhibition of growth |

In addition, the anaerobic ammonium oxidizing bacteria are extremely sensitive to dissolved oxygen concentration, as compared with other anaerobic microorganisms. Thus, the anaerobic ammonium oxidizing bacteria tend to cluster inside a membrane formed of the nitritation bacteria to avoid toxicity of dissolved oxygen and are mostly present in the form of granules having a size of 100 μm or more. Conversely, the heterotrophic denitrifying bacteria and the nitrifying bacteria are mostly present in the form of flocs having a size of less than 100 μm, for example, less than 80 μm due to high resistance to dissolved oxygen thereof and thus clearly differ in particle size and the like from the anaerobic ammonium oxidizing bacteria.

As a result of repeated experiments to improve nitrogen removal efficiency by continuously discharge heterotrophic denitrifying bacteria and nitrifying bacteria outside the bioreactor 1 while allowing anaerobic ammonium oxidizing bacteria and nitritation bacteria to be present in the bioreactor 1, the present inventors found that the aforementioned bacteria can be effectively separated through adjustment of the pore size of a mesh and nitrogen removal can be continuously performed by preventing pores of the mesh from being clogged by the anaerobic ammonium oxidizing bacteria, and thus completed the present invention.

In other words, in order to solve the problem that, in the process of selectively discharging heterotrophic denitrifying bacteria and nitrifying bacteria from a bioreactor through a continuous process using a filter, pores of a mesh are clogged by anaerobic ammonium oxidizing bacteria, causing reduction in efficiency in discharging the heterotrophic denitrifying bacteria and the nitrifying bacteria from the bioreactor 1, the present inventors invented a particle separation apparatus in which two flow paths having opposite effluent flow directions pass through a single filter (a first filter or a fourth filter) and a mesh or a blade assembly mounted on the first filter or the fourth filter is adapted to be rotatable, thereby enabling a continuous process in which anaerobic ammonium oxidizing bacteria having clogged pores of the mesh by hydraulic pressure from the bioreactor can be returned to the bioreactor 1 by hydraulic pressure into the bioreactor 1.

FIG. 1 is a diagram of a particle separation apparatus 1000 according to one exemplary embodiment of the present invention.

Referring to FIG. 1, the particle separation apparatus 1000 includes: a bioreactor 1 storing a sludge containing granular microorganisms; a first flow path 11 through which the sludge is discharged from the bioreactor 1; a first filter 100 including a first mesh 120 separating the granular microorganisms contained in the sludge discharged through the first flow path 11 according to size; a second flow path 12 into which an effluent having passed through the first filter 100 flows; a third flow path 13 connected to the second flow path 12 to discharge the effluent outside; a fourth flow path 14 connected to one side of the second flow path 12 and mounted on a surface of the first filter 100 connected to a surface of the first filter 100 with the second flow path 12 mounted thereon to circulate the effluent to the bioreactor 1; a fifth flow path 15 through which the effluent having been discharged from the fourth flow path 14 and passed through the first filter 100 flows into the bioreactor 1; and a first pump 10 creating a flow of the effluent, wherein the first mesh 120 is rotatably mounted on the first filter 100.

With the first mesh 120 rotatably mounted, the particle separation apparatus 1000 allows particles having clogged pores of the first mesh 120 by hydraulic pressure from the bioreactor 1 to be returned to the bioreactor 1 by hydraulic pressure into the bioreactor 1, thereby removing unnecessary particles from the bioreactor 1 through a continuous process.

The bioreactor 1 may store sewage or sludge and contain anaerobic ammonium oxidizing bacteria and the like and heterotrophic denitrifying bacteria and the like for biological nitrogen removal. As used herein, the term "anaerobic ammonium oxidizing bacteria and the like" refers to granules formed of anaerobic ammonium oxidizing bacteria and nitritation bacteria, and the term "heterotrophic denitrifying bacteria and the like" refers to bacteria including heterotrophic denitrifying bacteria and nitrifying bacteria other than the anaerobic ammonium oxidizing bacteria.

Specifically, the bioreactor 1 may perform deammonification and contain anaerobic ammonium oxidizing bacteria, nitritation bacteria, heterotrophic denitrifying bacteria, and nitrifying bacteria having different growth rates. The particle separation apparatus 1000 allows the heterotrophic denitrifying bacteria and the nitrifying bacteria to be continuously discharged from the bioreactor 1. Considering the growth rates of the aforementioned microorganisms, an appropriate sludge retention time (SRT) for each microorganism is as shown in Table 1.

The sludge stored in the bioreactor 1may be discharged from the bioreactor 1through the first flow path 11 and the first flow path 11 may be mounted on the first filter 100.

The first filter 100 may include the first mesh 120 separating the granular microorganisms contained in the sludge according to size and rotatably mounted thereon. The first mesh 120 may have a pore diameter of 50 μm or more, specifically 50 μm to 500 μm, for example, 100 μm to 500 μm.

As described above, when the first mesh 120 has a pore diameter of 50 μm or more, among the microorganisms having been discharged from the bioreactor 1through the first flow path 11, the anaerobic ammonium oxidizing bacteria can be controlled not to pass through the first filter 100 while allowing the heterotrophic denitrifying bacteria to pass through the first filter 100.

FIG. 2 and FIG. 3 are exploded perspective views of first filters 100, 300 according to exemplary embodiments of the present invention, respectively.

Referring to FIG. 2, the first filter 100 may include a first mesh cover 130 and a housing 110 in which the first mesh 120 is mounted, wherein the first mesh cover 130 may be disposed on both front and back surfaces of the first mesh 120 and the first mesh 120 may be settled between the two first mesh covers 130 by a first mesh cover cap 140 passing through a first mesh center groove 121 and a first mesh cover center groove 131.

The first mesh 120 may have a fan shape to be rotated by hydraulic pressure of the effluent from the bioreactor 1. Alternatively, a first mesh center groove 221 shaped to be engaged with a gear of a motor 60 may be provided such that a first mesh 220 can be rotated by the motor 60, as shown in FIG. 3. Examples of the particle separation apparatus 1000 configured such that the first mesh 220 can be rotated by the motor 60 are shown in FIG. 6 to FIG. 13.

FIG. 4 and FIG. 5 are views of housings according to exemplary embodiments of the present invention, specifically housings of the first filter 100 or 300 or a fourth filter 200 or 400, respectively.

Referring to FIG. 4 and FIG. 5, a first flow path connection 111 of the housing 500 or 600 may have a larger area than a fourth flow path connection 114 of the housing 500 or 600. In this way, the fourth flow path 14 has a smaller flow area and thus a higher effluent flow rate than the first flow path 11, whereby a continuous process for particle separation can be driven without supplying an excess of power to the pump.

Referring to FIG. 1 again, the effluent having passed through the first filter 100 may flow into the second flow path 12. Here, the effluent having passed through the first filter 100 contains the heterotrophic denitrifying bacteria, but little or no anaerobic ammonium oxidizing bacteria. Referring to FIG. 6, the particle separation apparatus 1000 may further include a sample collection valve 70 mounted on the second flow path 12 to perform component analysis on the microorganisms discharged from the bioreactor 1, specifically to analyze the presence or absence of the anaerobic ammonium oxidizing bacteria in an effluent having passed through the first filter 300 or the kinds and contents of the heterotrophic denitrifying bacteria and the like in the effluent, thereby preventing the anaerobic ammonium oxidizing bacteria from being discharged outside the bioreactor 1.

In addition, the second flow path 12 may be connected to the third flow path 13 through which the effluent is discharged from the particle separation apparatus 1000 and the fourth flow path through which the effluent flows into the first filter 100 to be returned to the bioreactor 1.

Referring to FIG. 7, the third flow path 13 is a passage through which the effluent is discharged from the particle separation apparatus 1000, and may include a sample collection valve 70 mounted thereon to perform component analysis on the microorganisms discharged from the particle separation apparatus 1000.

In this way, a user can analyze the presence or absence of the anaerobic ammonium oxidizing bacteria in an effluent discharged through the third flow path 13 or the kinds and contents of the heterotrophic denitrifying bacteria in the effluent.

Referring to FIG. 8, the particle separation apparatus 1000 may further include a second filter 40 disposed at a side of the second flow path 12 connected to the fourth flow path 14, wherein the second filter 40 may include a second mesh having a pore diameter of 1 μm to 50 μm to filter out the heterotrophic denitrifying bacteria and the like.

In addition, the second filter 40 may include a blade assembly 150 or 250 that is rotatably mounted on a surface of the second mesh, wherein the blade assembly 150 or 250 may include a rotary blade 160 or 260 and a cleaning brush 170 or 270 attached to one side of the blade 160 or 260, as described below. Here, the cleaning brush 170 or 270 may be rotated while contacting one surface of the first mesh 120 upon rotation of the blade 160 or 260.

In this way, the particle separation apparatus 1000 can allow heterotrophic denitrifying bacteria and like having been discharged from the bioreactor 1to be filtered out by the second filter 40 and prevented from flowing into the fourth flow path 14 while allowing the heterotrophic denitrifying bacteria and the like to be discharged from the particle separation apparatus 1000 through the second flow path 12 and the third flow path 13. In addition, with the blade assembly 150 or 250 provided to the second filter 40, the particle separation apparatus 1000 can prevent the second mesh from being clogged by the heterotrophic denitrifying bacteria and the like.

Referring to FIG. 9, the particle separation apparatus 1000 may further include a detention tank 2 storing an effluent having been discharged from the second flow path 12, such that the effluent from the detention tank 2 flows into the bioreactor 1through the fourth flow path 14 or is discharged from the particle separation apparatus 1000 through the third flow path In this way, the effluent can stay in the detention tank 2 before being discharged from the particle separation apparatus 1000 through the third flow path 13, whereby the proportion of the effluent returned to the bioreactor 1or separation efficiency can be improved, as compared with the case in which the effluent is immediately discharged from the particle separation apparatus 1000 through the third flow path 13 connected to one side of the second flow path.

Referring to FIG. 10, the particle separation apparatus 1000 may further include a third filter 50 disposed at an entrance of the fourth flow path 14 connected to the detention tank 2, wherein the third filter 50 may include a third mesh having a pore diameter of 1 μm to 50 μm.

In addition, the third filter 50 may include a blade assembly 150 or 250 that is rotatably mounted on a surface of the third mesh. The shape and effects of the blade assembly 150 or 250 may be the same as described in the second filter 40.

The fourth flow path 14 is connected to one side of the second flow path 12 and mounted on a surface of the first filter 100 connected to a surface of the first filter 100, on which the second flow path 12 is mounted, to circulate the effluent to the bioreactor 1. For example, the fourth flow path 14 may be mounted on the surface of the first filter 100, on which the second flow path 12 is mounted.

As used herein, the term "surface connected to . . . " may refer to any surface of one housing 110, 500, or 600 to which a corresponding flow path can be connected, regardless of a material forming the housings 110, 500, 600 of the first filter 100 or 300 or the fourth filter 200 or 400, without limitation. For example, when the first mesh 120 has a plate shape, the first flow path 11 and the fifth flow path 15 may be mounted on one surface of the first mesh 120, and the second flow path 12 and the fourth flow path 14 may be mounted on the other surface of the first mesh 120.

In this way, even when the pores of the first mesh 120 are clogged by the anaerobic ammonium oxidizing bacteria contained in the sludge discharged through the first flow path 11, with the first mesh 120 rotated, the particle separation apparatus 1000 can allow the effluent having passed through the fourth flow path 14 to pass through the first filter 100 toward the bioreactor 1, thereby forcing the anaerobic ammonium oxidizing bacteria having clogged the pores of the first mesh 120 to flow back into the bioreactor 1 through the fifth flow path 15.

The particle separation apparatus 1000 may further include a pump generating hydraulic pressure by which the sludge having been discharged from the bioreactor 1 and the effluent having passed through the first filter 100 can be discharged from the particle separation apparatus 1000 through the third flow path 13 or returned to the bioreactor 1.

Although the kind and position of the pump are not particularly limited, the pump may include one or more pumps connected to one or more of the first flow path 11, the second flow path 12, the third flow path 13, the fourth flow path 14, and the fifth flow path 15, respectively. For example, referring to FIG. 1, the first pump 10 may be connected to the second flow path 12. Alternatively, referring to FIG. 23, the first pump 10 may be connected to the first flow path 11.

Referring to FIG. 11 and FIG. 12, the particle separation apparatus 1000 may further include pumps other than the first pump 10. Specifically, referring to FIG. 11, the particle separation apparatus 1000 may further include a second pump 20 connected to the fourth flow path 14 upstream of the first filter 300. Referring to FIG. 12, the particle separation apparatus 1000 may further include a third pump 30 connected to the fifth flow path 15 upstream of the bioreactor 1. The particle separation apparatus 1000 as shown in FIG. 11 and FIG. 12 may also include the sample collection valve 70, the second filter 40, the third filter 50, and the detention tank 2 as described with reference to FIG. 6 to FIG. 10. For example, the particle separation apparatus 1000 may further include the second pump 20 and the detention tank 2, as shown in FIG. 24.

FIG. 13 is a diagram of a particle separation apparatus 2000 according to another embodiment of the present invention.

The particle separation apparatus 2000 includes: a bioreactor 1 storing a sludge containing granular microorganisms; a first flow path 11 through which the sludge is discharged from the bioreactor 1; a fourth filter 200 including a first mesh 120 separating the granular microorganisms contained in the sludge discharged through the first flow path 11 according to size and a blade assembly 150 rotatably mounted on a surface of the first mesh 120; a second flow path 12 through which an effluent having passed through the fourth filter 200 is discharged outside; a third flow path 13 connected to the second flow path 12 to discharge the effluent outside; a fourth flow path 14 connected to one side of the second flow path 12 and mounted on a surface of the fourth filter 200 connected to a surface of the fourth filter 200 with the second flow path 12 mounted thereon to circulate the effluent to the bioreactor 1; a fifth flow path 15 through which the effluent having been discharged from the fourth flow path 14 and passed through the first filter 100 flows into the bioreactor 1; and a first pump 10 generating a flow of the effluent, wherein the blade assembly 150 includes a rotary blade 160.

The particle separation apparatus 2000 is substantially the same as the particle separation apparatus 1000 except that the fourth filter 200 or 400 is provided instead of the first filter. Specifically, the particle separation apparatus 1000 includes the first mesh 120 which is rotatably mounted on the first filter 100 or 300, whereas the particle separation apparatus 2000 includes the fourth filter 200 or 400 which includes the blade assembly 150 mounted thereon to be rotatable on a surface of the first mesh 120.

Now, the fourth filter will be described in detail.

Referring to FIG. 14 and FIG. 15, the fourth filter 200 or 400 may include: the first mesh 120 separating the granular microorganisms contained in the sludge discharged through the first flow path 11 according to size; and the blade assembly 150 or 250 rotatably mounted on the surface of the first mesh 120.

Specifically, the blade assembly 150 or 250 includes a rotary blade 160 or 260 and a cleaning brush 170 or 270 attached to one side of the rotating blade 160 or 260, wherein the cleaning brush 170 or 270 may be rotated while contacting one surface of the first mesh 120 upon rotation of the blade 160 or 260.

Although the shape of the blade 160 or 260 is not particularly restricted, the blade 160 or 260 may be an axial blade wherein the flow-in direction of the sludge corresponds to the flow-out direction of the sludge. Thus, the blade 160 or 260 may be rotated by hydraulic pressure of the sludge discharged from the bioreactor 1 without any separate power unit for rotating the blade 160 or 260, as shown in FIG. 14. Alternatively, the blade 160 or 260 may be driven by a motor, as shown in FIG. 15. In addition, referring to FIG. 14 and FIG. 15, the blade 160 or 260 may include 1 to 4 blades, without being limited thereto.

When the blade 160 or 260 is rotated, the cleaning brush 170 or 270 is rotated on the surface of the first mesh 120 to sweep anaerobic ammonium oxidizing bacteria out of the pores of the first mesh 120, such that the anaerobic ammonium oxidizing bacteria can be returned to the bioreactor 1 by hydraulic pressure in the fifth flow path 15 after being drawn into a vortex inside the housing 110 of the fourth filter.

In accordance with another aspect of the present invention, there is provided a particle separation system including the particle separation apparatus 1000 or 2000, wherein the bioreactor 1 stores at least one granular microorganism selected from the group consisting of anaerobic ammonium oxidizing bacteria, heterotrophic denitrifying bacteria, nitritation bacteria, and nitrifying bacteria, and the granular microorganism is separated according to size to be discharged outside the bioreactor 1 or to be concentrated in the bioreactor 1.

The particle separation system contains granules formed of anaerobic ammonium oxidizing bacteria and nitritation bacteria. Here, during a nitrogen removal process, the anaerobic ammonium oxidizing bacteria, to which oxygen is highly toxic, may cluster within a membrane formed of the nitritation bacteria, as described above relating to the particle separation apparatus 1000 or 2000.

The particle separation system may be operated to prevent the granules formed of anaerobic ammonium oxidizing bacteria and nitritation bacteria from passing through the first mesh 120 or 220 while allowing the nitrifying bacteria to pass through the first mesh 120 or 220, such that the nitrifying bacteria can be continuously discharged from the bioreactor 1 while the anaerobic ammonium oxidizing bacteria can be concentrated in the bioreactor 1.

Preferably, the granules formed of anaerobic ammonium oxidizing bacteria and nitritation bacteria are concentrated in the bioreactor 1 such that the anaerobic ammonium oxidizing bacteria can remain dominant over the heterotrophic denitrifying bacteria. For example, 80 vol % or more, specifically 90 vol % or more of the granules may be concentrated in the bioreactor, based on the total volume of the granules.

Next, the present invention will be described in more detail with reference to examples. However, it should be noted that these examples are provided for illustration only and should not be construed in any way as limiting the invention. In addition, description of details apparent to those skilled in the art will be omitted for clarity.

PREPARATIVE EXAMPLE—PREPARATION OF BIOREACTOR 1

In order to implement a nitrogen removal process in which nitritation, anammox, and heterotrophic denitrification are continuously performed, a 10 L sequencing batch reactor was prepared, as shown in FIG. 16, and a system capable of real-time monitoring of ORP, DO, and pH was constructed, such that DO could be kept below 0.5 mg $O_2$/L automatically.

The bioreactor 1 was operated under conditions of a discharge rate of 33 vol % (based on the total volume of the bioreactor) and an initial hydraulic retention time of 10.5 hours. In order to increase a nitrogen removal rate, microorganisms were additionally implanted and then the hydraulic retention time in the bioreactor was adjusted to 0.84 days. One cycle consisted of 12 stepwise influent-injection sub-cycles. In each sub-cycle, the aeration time was controlled to sequentially induce heterotrophic denitrification, anammox, and partial nitritation.

In addition, in order to evaluate nitrogen removal performance with respect to an actual digested sludge supernatant, synthetic wastewater imitating the composition of the supernatant was prepared and introduced into the bioreactor 1.

TABLE 2

| | Concentration | |
|---|---|---|
| | Tap water (g/L) | Target conc. (g/L) |
| $(NH_4)_2SO_4$ | 0.15-2.36 | 0.700 |
| $NaHCO_3$ | 0.504 | 4.2 |
| CODCr as $C_6H_{12}O_6$ | — | 0.3 |
| $KH_2PO_4$ | 0.027 | 0.006 |
| $MgSO_4 7H_2O$ | 0.123 | 0.012 |
| $CaCl_2 2H_2O$ | 0.176 | 0.048 |
| Trace element solution I, II | 1 ml/L | |

EXAMPLES AND COMPARATIVE EXAMPLES

In order to evaluate microbial activity depending on the pore diameter of the first mesh, a sludge collected from a deammonification reactor was subjected to sequential sieving to obtain sludge samples, as shown in FIG. 18. A distribution of granular microorganisms implanted in the bioreactor 1 is shown in FIG. 19. A sludge sample obtained by collecting microorganisms remaining on a sieve with a pore size of 500 μm, a sludge sample obtained by collecting microorganisms remaining on a sieve with a pore size of 355 μm, a sludge sample obtained by collecting microorganisms remaining on a sieve with a pore size of 200 μm, a sludge sample obtained by collecting microorganisms remaining on a sieve with a pore size of 100 μm, a sample obtained by collecting microorganisms remaining on a sieve with a pore size of 50 μm, and a sample obtained by collecting microorganisms passing through the sieve with a pore size of 50 μm were referred to as "Comparative Example 1", "Example 1", "Example 2", "Example 3", "Example 4", and "Comparative Example 2", respectively.

Experimental Example 1: Comparison of Activity of Granular Microorganism

Activity of anaerobic ammonium oxidizing bacteria and heterotrophic denitrifying bacteria included in each of the sludge samples of Examples 1 to 4 and Comparative Examples 1 to 2 was measured. Specifically, the activity of anaerobic ammonium oxidizing bacteria was determined according to specific anammox activity (SAA) and the activity of heterotrophic denitrifying bacteria was determined according to specific nitrate utilization rate (SNUR), and evaluation results are shown in FIG. 20. In addition, the activity of nitrifying bacteria and nitritation bacteria was determined according to specific oxygen uptake rate (SOUR), and evaluation results are shown in FIG. 21.

Referring to FIG. 20, in each of the sludge sample of Example 4 (particle size: 50 μm to 100 μm) and the sludge sample of Comparative Example 2 (particle size: less than 50 μm), heterotrophic denitrifying bacteria were dominant over anaerobic ammonium oxidizing bacteria, whereas, in each of the sludge sample of Example 1 (particle size: 100 μm to 200 μm), the sludge sample of Example 2 (particle size: 200 μm to 355 μm), the sludge sample of Example 3 (particle size: 355 μm to 500 μm), and the sludge sample of Comparative Example 1 (particle size: greater than 500 μm), anaerobic ammonium oxidizing bacteria were dominant over heterotrophic denitrifying bacteria. Particularly, in sludge samples with particle sizes of 200 μm or more, heterotrophic denitrifying bacteria were hardly activated.

Therefore, it can be seen that, when the first mesh 120 or 220 of the particle separation apparatus 1000 or 2000 according to the invention has a pore size of 100 μm or more, anaerobic ammonium oxidizing bacteria can be dominant in the bioreactor 1 while heterotrophic denitrifying bacteria can be discharged outside the bioreactor 1 through the first mesh 120 or 220, and, when the first mesh 120 or 220 has a pore size of 200 μm or more, heterotrophic denitrifying bacteria hardly remain in the bioreactor 1.

In addition, referring to FIG. 21, it can be seen that in each of the sludge samples of Examples 1 to 4 and Comparative Examples 1 to 2, nitritation bacteria were dominant over nitrifying bacteria. Particularly, it can be seen that, when the first mesh 120 or 220 having a pore size of 200 μm is used, nitrifying bacteria exhibit extremely low activity and thus can be sufficiently discharged outside the bioreactor 1. In addition, it can be seen that, in each of the sludge sample with a particle size of less than 100 μm and the sludge sample with a particle size of less than 50 μm, the activity of nitrifying bacteria was almost unchanged and the activity of nitritation bacteria was reduced, as compared with those of the other sludge samples.

Therefore, it can be seen that, when the first mesh 120 or 220 of the particle separation apparatus 1000 or 2000 according to the invention has a pore size of 50 μm or more, operation conditions of the particle separation apparatus 1000 or 2000 can be easily controlled according to conditions of the bioreactor 1, for example, the temperature or property change of a sludge contained in the bioreactor 1. As shown in FIG. 20 and FIG. 21, since, when granular microorganisms have a particle size of less than 100 μm or less than 50 μm, the activity of heterotrophic denitrifying bacteria and nitrifying bacteria remains almost unchanged and the activity of anaerobic ammonium oxidizing bacteria and nitritation bacteria is greatly reduced, as compared with when granular microorganisms have a particle size of 100 μm or more, operating conditions of the particle separation apparatus can be easily controlled by adjusting the pore size of the first mesh 120 or 220 within the range of 50 μm to 100 μm depending upon the proportion of microorganisms to be discharged from the bioreactor 1and, ultimately, from the particle separation apparatus 1000 or 2000, determined according to SRT shown in Table 1, without changing other conditions.

Experimental Example 2: Comparison of Degree of Concentration Between Anaerobic Ammonium Oxidizing Bacteria and Heterotrophic Denitrifying Bacteria A degree of concentration of microorganisms by sieving was measured for each of the sludge samples of Examples 1 to 3 and Comparative Example 1 based on cumulative activity of anaerobic ammonium oxidizing bacteria and heterotrophic denitrifying bacteria contained in each sludge sample. Results are shown in FIG. 22.

Referring to FIG. 22, in the sludge samples of Examples 1 to 3 and Comparative Example 1 having a particle size of 100 it can be seen that 95.7 vol % of the anaerobic ammonium oxidizing bacteria and 34.7 vol % of the heterotrophic denitrifying bacteria were concentrated by sieving, based on the total volume of a corresponding microorganism.

Therefore, it can be seen that, when the first mesh 120 or 220 of the particle separation apparatus 1000 or 2000 according to the invention has a pore size of 100 μm or more, anaerobic ammonium oxidizing bacteria can be separated and concentrated in high yield in the bioreactor 1.

Although some embodiments have been described herein, it should be understood that these embodiments are provided for illustration only and are not to be construed in any way as limiting the present invention, and that various modifications, changes, alterations, and equivalent embodiments can be made by those skilled in the art without departing from the spirit and scope of the invention. The scope of the present invention should be defined by the appended claims and equivalents thereof.

LIST OF REFERENCE NUMERALS

1: bioreactor
2: detention tank
10: first pump
20: second pump
30: third pump
40: second filter
50: third filter
60: motor
70: sample collection valve
11: first flow path
12: second flow path
13: third flow path
14: fourth flow path
15: fifth flow path
100, 300: first filter
200, 400: fourth filter
110, 500, 600: housing
120, 220: first mesh
121, 221: first mesh center groove
130: first mesh cover
131: first mesh cover center groove
140, 240: first mesh cover cap
111: first flow path connection hole
112: second flow path connection hole
114: fourth flow path connection hole
115: fifth flow path connection hole
150, 250: blade assembly
160, 260: blade
170, 270: cleaning brush

The invention claimed is:

1. A particle separation apparatus, comprising:
a bioreactor storing a sludge containing granular microorganisms;
a first flow path through which the sludge is discharged from the bioreactor;
a first filter comprising a first mesh separating the granular microorganisms contained in the sludge discharged through the first flow path according to size;
a second flow path into which an effluent having passed through the first filter flows;
a third flow path connected to the second flow path to discharge the effluent outside;
a fourth flow path connected to one side of the second flow path and mounted on a first portion of a surface of the first filter, the first portion being connected to a second portion of the surface of the first filter on which the second flow path is mounted to circulate the effluent to the bioreactor;
a fifth flow path through which the effluent having been discharged from the fourth flow path and passed through the first filter flows into the bioreactor; and
a first pump creating a flow of the effluent,
wherein the first mesh unit is rotatably mounted on the first filter.

2. The particle separation apparatus according to claim 1, wherein the first mesh has a pore diameter of 50 μm to 500 μm.

3. The particle separation apparatus according to claim 1, wherein a first flow path connection connected to one side of the first filter has a larger area than a second flow path connection connected to one side of the first filter.

4. The particle separation apparatus according to claim 1, wherein the second flow path contacts the first pump.

5. The particle separation apparatus according to claim 4, further comprising:
a second pump disposed on the fourth flow path upstream of the first filter.

6. The particle separation apparatus according to claim 5, further comprising:
a third pump disposed on the fifth flow path upstream of the bioreactor.

7. The particle separation apparatus according to claim 1, further comprising:

a detention tank storing the effluent discharged from the second flow path such that the effluent from the detention tank flows into the bioreactor through the fourth flow path or is discharged from the particle separation apparatus through the third flow path.

8. The particle separation apparatus according to claim 1, further comprising:
a sample collection valve mounted on the second flow path to perform component analysis on the microorganisms discharged from the bioreactor.

9. The particle separation apparatus according to claim 1, wherein the first filter further comprises a blade assembly secured to a surface of the first mesh.

10. A particle separation system comprising the particle separation apparatus according to claim 1, wherein the granular microorganisms comprise at least one selected from the group consisting of anaerobic ammonium oxidizing bacteria, heterotrophic denitrifying bacteria, nitritation bacteria, and nitrifying bacteria, and the particle separation system separates the granular microorganisms according to size and allows the separated granular microorganisms to be discharged outside the bioreactor or to be concentrated in the bioreactor.

11. The particle separation system according to claim 10, wherein the granular microorganisms comprise granules formed of the anaerobic ammonium oxidizing bacteria and the nitritation bacteria, and the particle separation system is operated to prevent the granules formed of the anaerobic ammonium oxidizing bacteria and the nitritation bacteria from passing through the first mesh while allowing the nitrifying bacteria to pass through the first mesh.

12. A particle separation apparatus, comprising:
a bioreactor storing a sludge containing granular microorganisms;
a first flow path through which the sludge is discharged from the bioreactor;
a first filter comprising a first mesh separating the granular microorganisms contained in the sludge discharged through the first flow path according to size and a blade assembly rotatably mounted on a surface of the first mesh;
a second flow path through which an effluent having passed through the first filter is discharged outside;
a third flow path connected to the second flow path to discharge the effluent outside;
a fourth flow path connected to one side of the second flow path and mounted on a first portion of a surface of the first filter, the first portion being connected to a second portion of the surface of the first filter on which the second flow path is mounted to circulate the effluent to the bioreactor;
a fifth flow path through which the effluent having been discharged from the fourth flow path and passed through the first filter flows into the bioreactor; and
a first pump creating a flow of the effluent,
wherein the blade assembly comprises a rotary blade.

13. The particle separation apparatus according to claim 12, wherein the blade assembly comprises a cleaning brush attached to one side of the blade, the cleaning brush being adapted to be rotated while contacting one surface of the first mesh upon rotation of the blade.

14. The particle separation apparatus according to claim 12, wherein a first flow path connection connected to one side of the first filter has a larger area than a second flow path connection connected to one side of the first filter.

15. The particle separation apparatus according to claim 12, further comprising:
a second pump disposed on the fourth flow path upstream of the first filter.

16. The particle separation apparatus according to claim 12, wherein the first mesh has a pore diameter of 50 μm to 500 μm.

17. The particle separation apparatus according to claim 12, wherein the second flow path contacts the first pump.

18. The particle separation apparatus according to claim 12, further comprising:
a detention tank storing the effluent discharged from the second flow path such that the effluent from the detention tank flows into the bioreactor through the fourth flow path or is discharged from the particle separation apparatus through the third flow path.

19. A particle separation system comprising the particle separation apparatus according to claim 12, wherein the granular microorganisms comprise at least one selected from the group consisting of anaerobic ammonium oxidizing bacteria, heterotrophic denitrifying bacteria, nitritation bacteria, and nitrifying bacteria, and the particle separation system separates the granular microorganisms according to size and allows the separated granular microorganisms to be discharged outside the bioreactor or to be concentrated in the bioreactor.

20. The particle separation system according to claim 19, wherein the granular microorganisms comprise granules formed of the anaerobic ammonium oxidizing bacteria and the nitritation bacteria, and the particle separation system is operated to prevent the granules formed of the anaerobic ammonium oxidizing bacteria and the nitritation bacteria from passing through the first mesh while allowing the nitrifying bacteria to pass through the first mesh.

* * * * *